United States Patent [19]

Baker

[11] Patent Number: 5,665,894
[45] Date of Patent: Sep. 9, 1997

[54] INSTRUMENT CALIBRATING DEMAND FLOW REGULATOR

[75] Inventor: George D. Baker, Cambridge, Md.

[73] Assignee: Air Liquide America Corporation, Houston, Tex.

[21] Appl. No.: 609,833

[22] Filed: Mar. 1, 1996

[51] Int. Cl.⁶ .................................................. G01N 31/00
[52] U.S. Cl. ................. 73/1.05; 137/614.19; 137/614.21; 137/907; 73/1.06
[58] Field of Search ..................... 73/1 G; 137/DIG. 907, 137/614.19, 614.21

[56] References Cited

U.S. PATENT DOCUMENTS

| | | |
|---|---|---|
| 3,467,137 | 9/1969 | Brown . |
| 3,633,611 | 1/1972 | MacNiel . |
| 4,140,113 | 2/1979 | Pedersen . |
| 4,214,580 | 7/1980 | Pedersen . |
| 4,921,006 | 5/1990 | Evans ........................ 137/907 |
| 4,977,776 | 12/1990 | Shindo et al. ................. 73/1 G |
| 5,343,858 | 9/1994 | Winefordner et al. . |
| 5,520,170 | 5/1996 | Laswick et al. . |

*Primary Examiner*—Robert Raevis
*Attorney, Agent, or Firm*—Burns, Doane, Swecker and Mathis

[57] ABSTRACT

An instrument calibrating demand flow regulator for providing a demanded amount of calibration gas from a calibration gas source to an instrument to be calibrated to permit calibration of the instrument includes a housing having an interior, an inlet for connection to the calibration gas source and an outlet for connection to the instrument to be calibrated. A pressure regulating valve device positioned within the interior of the housing regulates the pressure of the calibrated gas entering the interior of the housing through the inlet and a demand flow valve device delivers calibration gas to the outlet of the housing upon demand by a pump operatively associated with the instrument.

20 Claims, 4 Drawing Sheets

INSTRUMENT CALIBRATING DEMAND FLOW REGULATOR

FIELD OF THE INVENTION

The present invention relates to the calibration of instruments and more particularly to an instrument calibrating demand flow regulator that is adapted to be interconnected between a source of calibration gas and an instrument to be calibrated to deliver calibration gas in response to the demand requirements of the instrument.

BACKGROUND OF THE INVENTION

Detection units or instruments are used in a wide variety of different fields to detect the presence of a gas or the presence of a gas in a particular amount. The gas is oftentimes hazardous in nature so that its presence in a particular area can pose a significant health risk. Underground parking garages, for example, are susceptible to the accumulation of potentially dangerous levels of carbon monoxide as a result of vehicular travel in the garage. Similarly, manufacturing facilities that utilize or produce harmful gases in connection with the production of products or in other contexts are susceptible of potential problems should a leak develop in the gas delivery system. Underground mines, manholes and other confined space entries represent other contexts in which similar concerns arise.

In these as well as a wide range of other settings, it is important to be able to determine the existence of the gas or potentially harmful levels of the gas and for this reason appropriate gas detecting instruments are utilized. When the level of gas in the area reaches a certain level, the instrument provides an appropriate indication such as by emitting a noise or providing some other suitable signal.

These instruments, which typically include their own suction pump, require regular calibration to ensure proper and accurate operation. This typically entails the use of a calibration gas which is introduced into the instrument. At present, there are several different techniques employed for calibrating an instrument through use of a calibration gas. One mechanism involves the use of a sample bag into which a desired amount of calibration gas is transferred from the calibration gas source (e.g., gas cylinder). The sample bag containing the calibration gas is then connected to the instrument to be calibrated. The suction pump associated with the instrument draws the calibrated gas out of the sample bag and into the instrument to be calibrated to thereby permit calibration of the instrument. Unfortunately, the use of a sample bag presents a variety of disadvantages and drawbacks.

In one respect, it is typically necessary to employ some additional piece of equipment such as a regulator to transfer the gas from the gas source to the sample bag and this of course requires additional equipment. Also, while calibration gas is being transferred to the sample bag, care must be taken to prevent contamination of the calibration gas. Typically, this sample bag is repeatedly purged in an attempt to cleanse the bag, but this results in gas being wasted.

In addition, it is not uncommon for the sample bag to become ripped or torn, or to simply wear out rather regularly. This adds to the cost associated with this type of calibration procedure. Operator training is also important since the operator must perform a variety of manual steps to prevent contamination and ensure accurate calibration of the instrument. This training can be expensive and time consuming, and still may not eliminate the possibility of contamination or inaccurate calibration.

Another way of effecting the necessary calibration involves permitting calibration gas to flow from the calibration gas cylinder into a "T" at a rate that exceeds the requirement of the instrument to be calibrated. One leg of the "T" is left open to the atmosphere to vent the excess gas while the other leg of the "T" is connected to the instrument to be calibrated. The instrument pump then pumps the gas into the instrument so that the instrument can be calibrated.

This technique also suffers from the disadvantage that additional equipment such as a regulator is required to transfer the gas from the calibration gas cylinder to the instrument. Also, care must once again be taken to prevent contamination in the transfer process and if the flow rate is not higher than the instrument demand, an error in calibration can arise. Also, since the rate of flow of the calibration gas exceeds the instrument requirements, calibration gas is needlessly wasted. Further, the operator must activate and deactivate the calibration gas delivery system to effect calibration of the instrument.

In light of the foregoing, a need exists for a way of calibrating an instrument in a way that addresses the foregoing disadvantages and drawbacks. In one respect, it would be desirable to provide a way of calibrating instruments that eliminates the relatively complex operator training associated with other known calibration techniques. A need also exists for a mechanism that facilitates the transfer of calibration gas from the calibration gas source to the instrument to be calibrated without needlessly wasting calibration gas. It would also be desirable to provide a mechanism that provides the possibility for unattended automatic instrument calibration.

SUMMARY OF THE INVENTION

In light of the foregoing, according to one aspect of the invention, a calibration system for calibrating an instrument includes a source of calibration gas, and a housing having an interior, an inlet connected to the source of calibration gas, and an outlet for connection to the instrument to be calibrated. A movable element preferably in the form of a diaphragm is disposed within the interior of the housing and movable in response to a pressure differential on opposite sides of the movable element. A demand flow valve element is positioned within the interior of the housing to form a first space within the interior between the movable element and the demand flow valve element. A pressure regulating valve device disposed within the interior of the housing forms a second space within the housing interior between the demand flow valve element and the pressure regulating valve device. The demand flow valve element is movable between one position in which gas flow between the first space and the second space is prevented and a second position in which gas flow between the first space and the second space is permitted. The demand flow valve element is operatively associated with the movable element so that movement of the movable element caused by a pressure differential across the movable element results in movement of the demand flow valve element from the first position to the second position. The pressure regulating valve element is movable between a first position in which the flow of calibration gas into the second space is prevented and a second position in which the flow of calibration gas into the second space is permitted. The pressure regulating valve element moves from the first position to the second position in response to the pressure in the second space being reduced to a predetermined level after the demand flow valve has moved away from the first position.

According to another aspect of the present invention, an instrument calibrating demand flow regulator for providing a demanded mount of calibration gas from a calibration gas source to an instrument to be calibrated to permit calibration of the instrument includes a housing having an interior, an inlet for connection to the calibration gas source and an outlet for connection to the instrument to be calibrated. A pressure regulating valve device positioned within the interior of the housing regulates the pressure of the calibrated gas entering the interior of the housing through the inlet and a demand flow valve device delivers calibration gas to the outlet of the housing upon demand by a pump operatively associated with the instrument.

In accordance with a further aspect of the invention, a method of calibrating an instrument involves connecting an inlet of an instrument calibrating demand flow regulator to a calibration gas source, with the instrument calibrating demand flow regulator including a pressure regulating valve device positioned within the interior of a housing for regulating the pressure of calibration gas entering the housing interior through the inlet and a demand flow valve device positioned within the interior of the housing for delivering calibration gas to an outlet of the housing upon demand by a suction pump associated with the instrument. The instrument to be calibrated is connected to the outlet of the housing so that the pump of the instrument to be calibrated draws calibrated gas through the instrument calibration demand flow regulator.

BRIEF DESCRIPTION OF THE DRAWING FIGURES

DETAILED DESCRIPTION OF THE INVENTION

The instrument calibrating demand flow regulator of the present invention provides a relatively compact light-weight mechanism for use in transferring calibration gas from the calibration gas source to the instrument to be calibrated. The device advantageously possesses a low dead volume and relatively quick response time, and eliminates the need for time consuming and complex operator training. Additionally, the device eliminates calibration gas wastage during the calibration procedure and also provides a mechanism for allowing unattended automatic calibration procedures when used in connection with an appropriate valving system and instrument control system.

The instrument calibrating demand flow regulator according to the present invention is designed to be connected between a source of calibration gas and the instrument to be calibrated. Generally speaking, the device is provided with a pressure regulating portion that reduces the gas pressure from the calibration gas source to a desired level. Another portion of the instrument calibrating demand flow regulator detects the gas demand of the instrument to be calibrated and then meets that demand by providing the appropriate mount of calibration gas.

Figure 1:
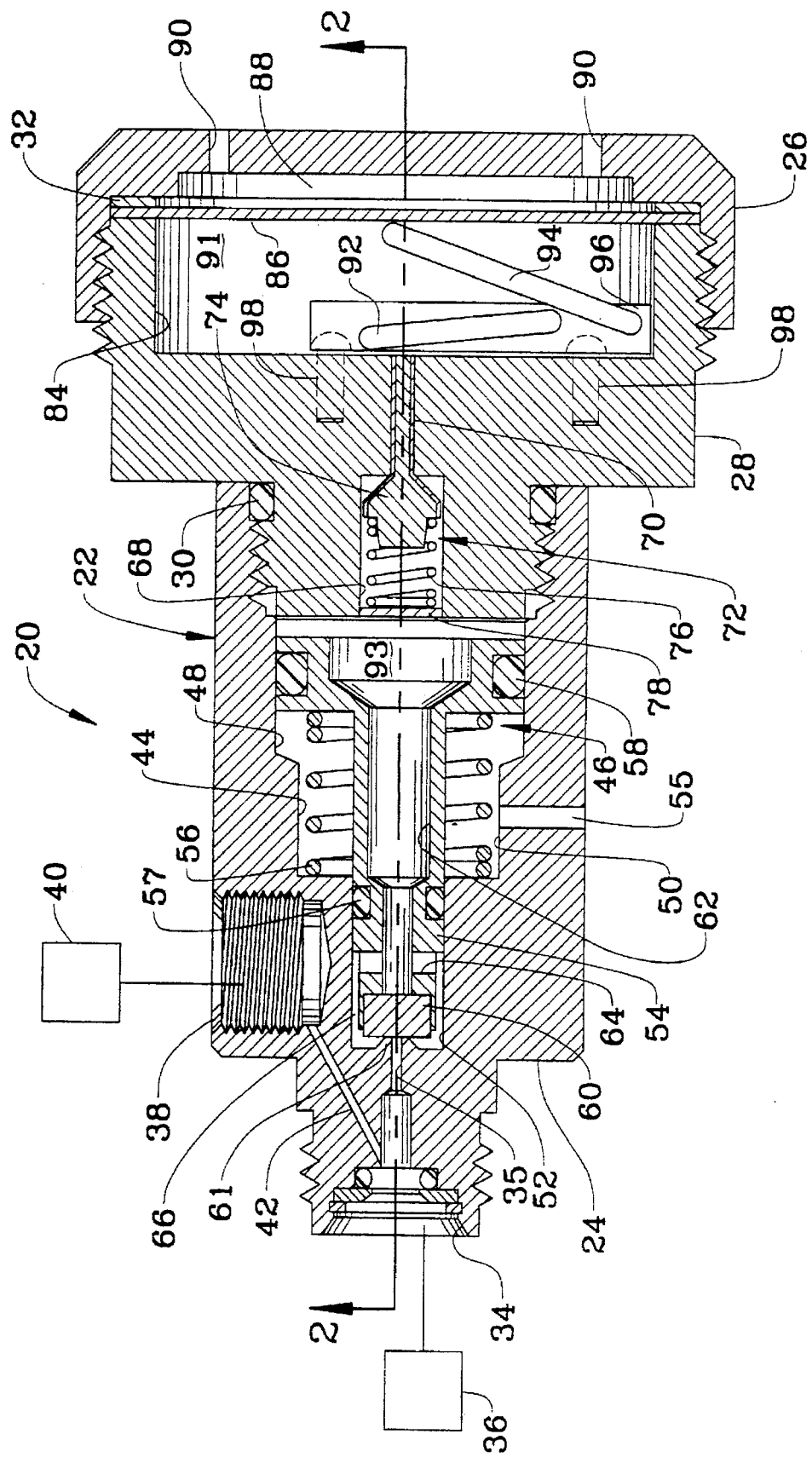
FIG. 1 is a longitudinal cross-sectional view of an instrument calibrating demand flow regulator in accordance with one embodiment of the present invention.
Figure 2:
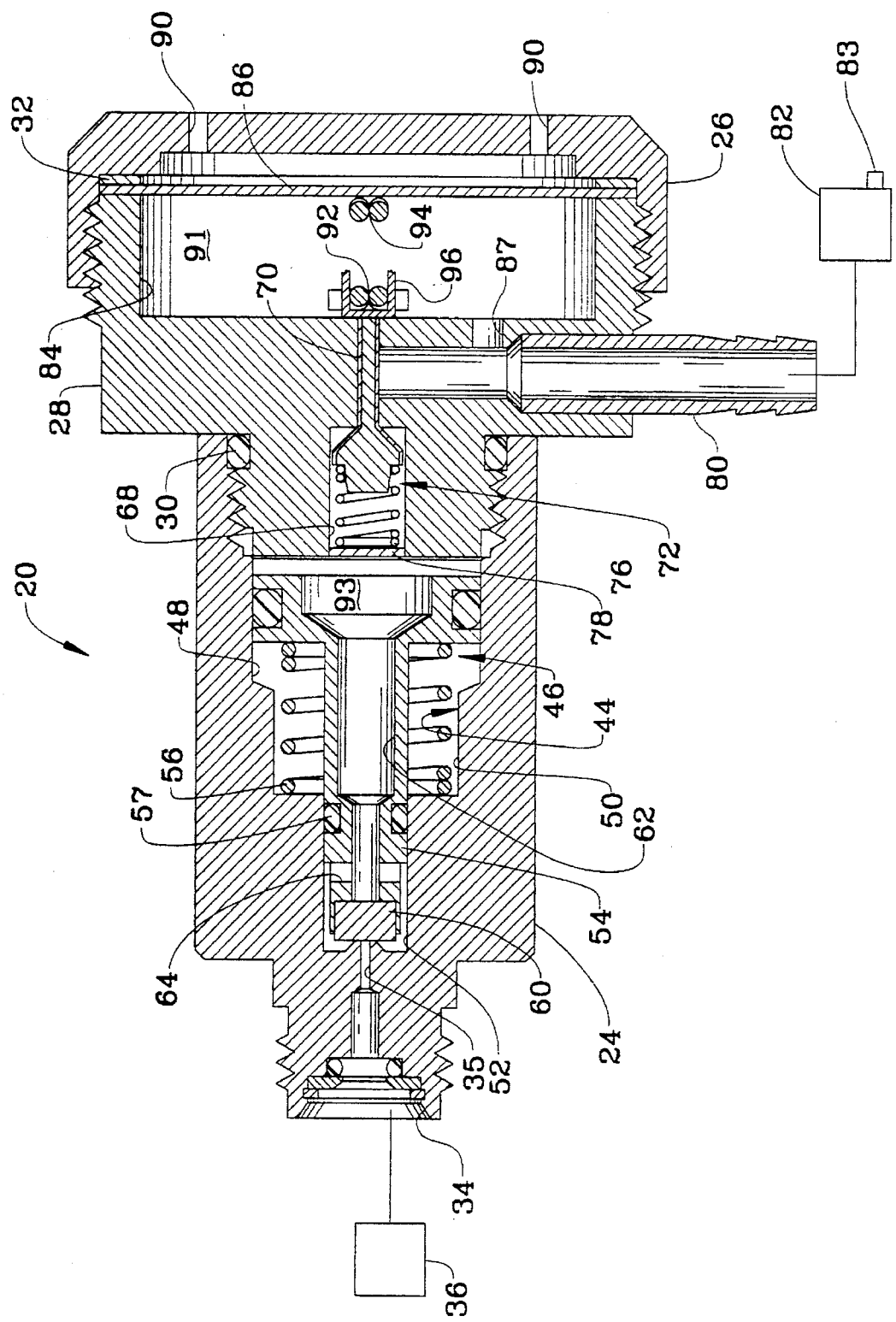
FIG. 2 is a longitudinal cross-sectional view of the instrument calibrating demand flow regulator shown in FIG. 1 taken along the section line 2—2.

With reference initially to FIGS. 1 and 2 which illustrate one embodiment of the present invention, the instrument calibrating demand flow regulator 20 includes a housing 22 which in the illustrated embodiment includes a first housing end section 24, a second housing end section 26 and an intermediate housing section 28. One end of the first housing section 24 is provided with internal threads that threadably engage external threads on one end of the intermediate housing section 28. A seal element 30 is disposed between the first end section 24 and the intermediate section 28 to provide a fluid tight seal between the two housing sections 24, 28. The opposite end of the intermediate housing section 28 is provided with external threads that engage internal threads on the second end section 26. A slip ring element 32 is disposed between the intermediate housing section 28 and the second end section 26.

One end of the first housing end section 24 is provided with an inlet 34. As schematically illustrated in FIGS. 1 and 2, the inlet 34 is adapted to be connected to a source of calibration gas 36. The calibration gas source 36 can be a cylinder or other appropriate source of calibration gas. The first housing end section 24 is also provided with an internally threaded gauge port 38. As schematically illustrated in FIG. 1, the gauge port 38 is adapted to be connected to a gauge 40 which measures or determines the pressure in the calibration gas source 36 and provides a display of the pressure. The gauge port 38 is connected to the inlet 34 by way of a connecting passage 42 that extends through the first housing section 24.

The first housing end section 24 is provided with a bore 44 that receives a pressure regulating valve element 46. The bore 44 includes a large diameter bore section 48 that tapers into an intermediate bore section 50 of smaller internal diameter which in turn merges into a small diameter bore section 52. The small diameter bore section 52 communicates with the inlet 34 at the end of the first housing section 24.

The pressure regulating valve element 46 includes a piston 54 that is spring-biased away from the inlet 34 by way of a spring 56. The piston 54 is provided with two annular grooves that each receive a respective annular seal ring 57, 58 for purposes of effecting a fluid tight seal with the interior of the bore 44 at two spaced apart locations. The space between the outer periphery of the piston 54 and the inner surface of the bore 44 which is delimited by the two seal rings 57, 58 is in communication with the atmosphere by way of a through hole 55 in the first housing section 24.

The piston 54 is also provided with a larger diameter end located furthest distally from the inlet 34 and a smaller diameter end located proximally the inlet 34. The end of the piston 54 closest to the inlet 34 (i.e., the smaller diameter end) is provided with a seal 60 which can be in the form of a teflon disk. The seal 60 is adapted to engage a seat 60 formed in the small diameter bore section 52 of the bore 44.

The piston 54 also includes a longitudinally extending through bore 62 extending from the large diameter end of the piston 54 towards the oppositely located small diameter end of the piston 54. The small diameter end of the piston 54 is provided with a cross bore 64 that is disposed transverse to the longitudinally extending through bore 62 and communicates with the longitudinally extending cross bore 62.

As can be seen in FIGS. 1 and 2, the smaller diameter end of the piston 54 located adjacent the inlet 34 is provided with a reduced outside diameter portion so that a space 66 exists between the outer peripheral surface of that portion of the piston 54 and the inner surface of the small diameter bore section 52. As a result, when the seal 60 moves away from the seat 61 that is located at the end of the small diameter bore section 52, gas from the calibration gas source 36 is able to flow through the inlet 34, through the space 66, through the cross bore 64 and into the through bore 62 of the piston 54.

The intermediate housing section 28 is provided with a through bore that includes a larger diameter bore portion 68 and a smaller diameter bore portion 70. Disposed within the through bore in the intermediate housing section 28 is a demand flow valve element 72. The demand flow valve element 72 includes a conical poppet valve 74 and a spring 76 that urges the poppet valve 74 in the direction away from the pressure regulating valve element 46. The poppet 74 is provided with a rubber or other elastomeric-type cover that is adapted to provide a seal with the transition between the larger diameter bore portion 68 and the smaller diameter bore portion 70 of the intermediate housing section 28. The spring 76 is disposed between the poppet 74 and a centrally apertured press-fit washer 78.

As seen specifically in FIG. 2, the intermediate housing section 28 is also provided with an outlet 80 that communicates with the smaller diameter bore portion 70 of the intermediate housing section 28. As schematically illustrated in FIG. 2, the outlet 80 is adapted to be connected to the instrument 82 that is to be calibrated, which instrument 82 is typically provided with a suction pump 83.

A recess 84 is formed in the end of the intermediate housing section 28 that is remote from the inlet 34. Positioned between the second housing end section 26 and the intermediate housing section 28 is a flexible diaphragm 86. The diaphragm 86 provides a seal between the two housing sections 26, 28. Also a space 88 is defined between the flexible diaphragm 86 and the second housing end section 26, and this space 88 communicates with the atmosphere by way of a plurality of through holes 90 provided in the second housing end section 26.

Positioned within the recess 84 in the intermediate housing section 28 is a first pivotally mounted lever member 92 and a second pivotally mounted lever member 94. The first lever member 92 is disposed so as to be generally positioned between the second lever member 94 and the poppet valve 74. The second lever member 94 is generally positioned between the flexible diaphragm 86 and the first lever member 92. The first lever member 92 is biased towards the diaphragm 86 by the spring biased poppet valve 74, and the second lever member 94 is biased towards the diaphragm 86 by the first lever member 92. The lever members 92, 94 are pivotally mounted on a mounting bracket 96 which, as shown in FIG. 1, is connected to the intermediate housing section 28 by connecting screws 98. The poppet 74 in conjunction with the spring 76, the diaphragm, the and the lever member 92, 94 define a demand flow valve device.

By virtue of the above-described construction of the instrument calibrating demand flow regulator, a first space 91 is defined within the housing 22 between the demand flow valve element 72 and the flexible diaphragm 86. In addition, a second space 93 is defined within the housing between the demand flow valve element 72 and the pressure regulating valve element 46. The first space 91 is connected to the outlet 80 by way of a through opening 87 in the intermediate housing section 28.

The instrument calibrating demand flow regulator shown in FIGS. 1 and 2 depicts the position of the various parts of the regulator prior to connection to the instrument to be calibrated. The regulator is designed so that when connected to the calibration gas source, the total force acting towards the right (i.e., the force associated with the calibration gas source combined with the spring force associated with the spring 56) is less than the total force acting towards the left. This is accomplished by appropriately sizing the bore 62 in the piston 54, by providing a spring having a desired spring constant and by appropriately sizing the passage 35 at the end of the inlet 34.

In operation, the instrument calibrating demand flow regulator 20 is connected to the calibration gas source 36 to provide a source of calibration gas while the outlet 80 is connected to the instrument 82 to be calibrated. The operation of the pump 83 associated with the instrument to be calibrated 82 causes a drop in pressure in the first space 91 which thus causes the diaphragm 86 to move inwardly towards the demand flow valve element 72. The movement of the flexible diaphragm 86 effects a pivoting movement of the second lever member 94 towards the first lever member 92 which in turn causes the first lever member 92 to contact the poppet valve 74 and slidably move the poppet valve 74 in opposition to the biasing force of the spring 76. This produces communication between the first space 91 and the second space 93 so that the second space 93 is subjected to the reduced pressure. As a result, the piston 54 to move rightward so that the seal 60 becomes unseated from the seat 61 at the end of the bore 44 in the first housing end section 24. Calibration gas from the calibration gas source 36 then flows into the inlet 34, through the space 66 between the inner surface of the small diameter bore section 52 and the outer periphery of the end of the piston 54, through the cross bore 64, through the longitudinally extending bore 62 in the piston 54, through the larger and smaller diameter bore portions 68, 70 in the intermediate housing section 28, and through the outlet 80 to the instrument to be calibrated 82. The amount of calibration gas delivered to the instrument 82 to be calibrated equals the amount demanded by the instrument pump 83 and once the instrument 82 is disconnected from the outlet 80, the flow of calibration gas automatically ceases. That is, upon disconnection of the instrument 82 from the outlet 80, the flexible diaphragm 86 moves back to the position shown in FIGS. 1 and 2 as a result of the pressure equalization in the spaces 88, 91 on either side of the diaphragm 86. The lever members 92, 94 thus return to the position illustrated in FIG. 1 as a result of the movement of the spring-biased poppet valve 74 to the seated position illustrated in FIGS. 1 and 2. This then causes the piston 54 to also return to the illustrated position shown in FIGS. 1 and 2.

It can be seen, therefore, that the instrument calibrating demand flow regulator of the present invention is a two stage system in which the left part illustrated in the drawing figure serves as a pressure regulator that accepts the calibration gas under the pressure conditions existing at the source and reduces it to a predetermined pressure. The pressure in the calibration gas source can be on the order of 2200 psi and that pressure is reduced to a predetermined level which can be on the order of 30–50 psi. The second stage defined by the right-side portion of the regulator in the drawing figures is designed to detect the demand of the instrument to be calibrated and to meet such demand through movement of the flexible diaphragm 86, the lever elements 92, 94 and the poppet valve 74.

The instrument calibrating demand flow regulator 20 in accordance with the present invention is designed to provide a maximum gas flow rate of 6.0 liters/min., with a typical flow rate being on the order of 0.2–2.0 liters/min. This relatively low flow rate is indicative of the particular context in which the demand flow regulator of the present invention is used since the calibration of instruments typically does not require a large flow rate to effect the necessary calibration of the instrument.

Figure 3:
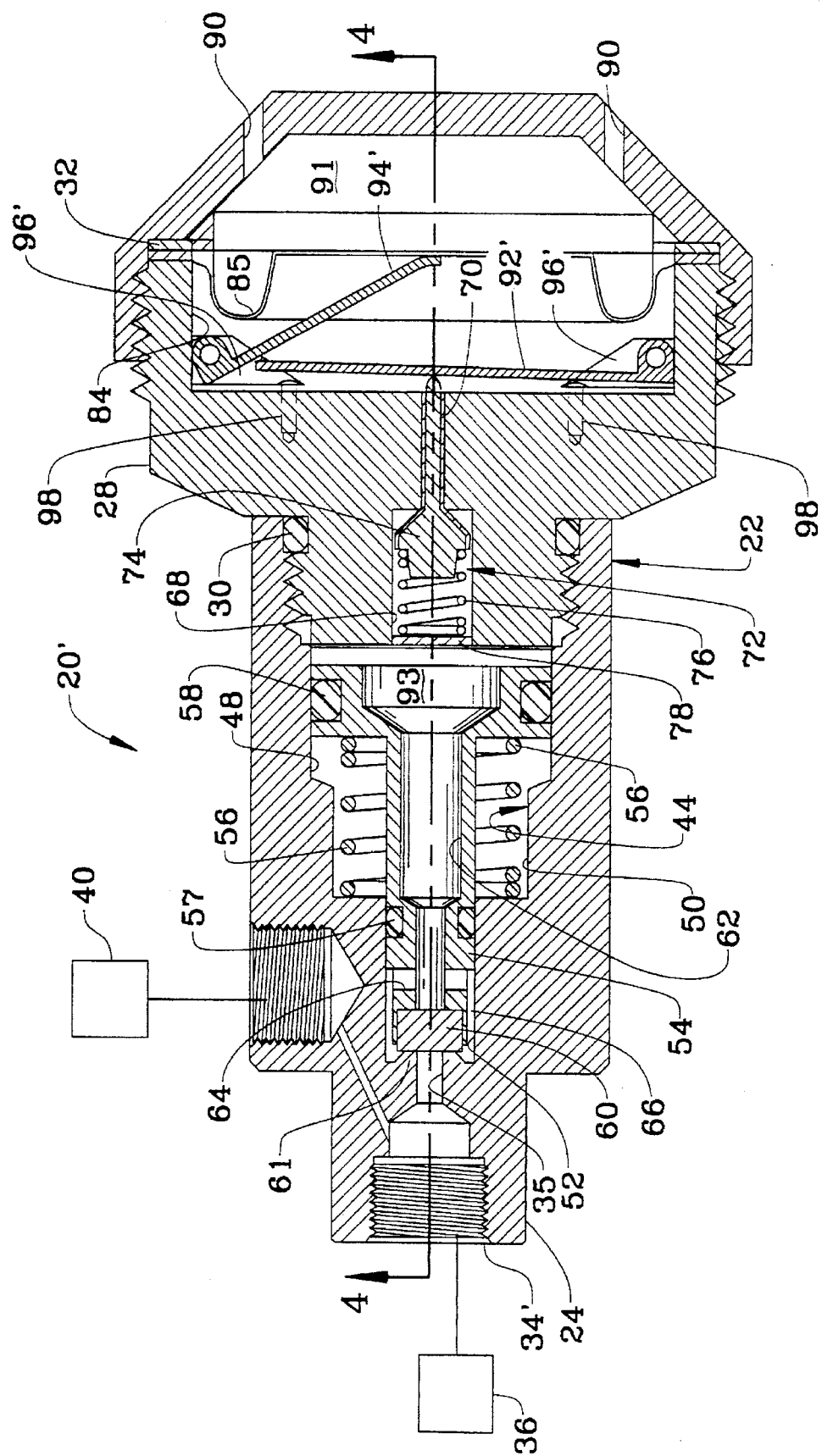
FIG. 3 is a longitudinal cross-sectional view of an instrument calibrating demand flow regulator in accordance with another embodiment of the present invention.
Figure 4:
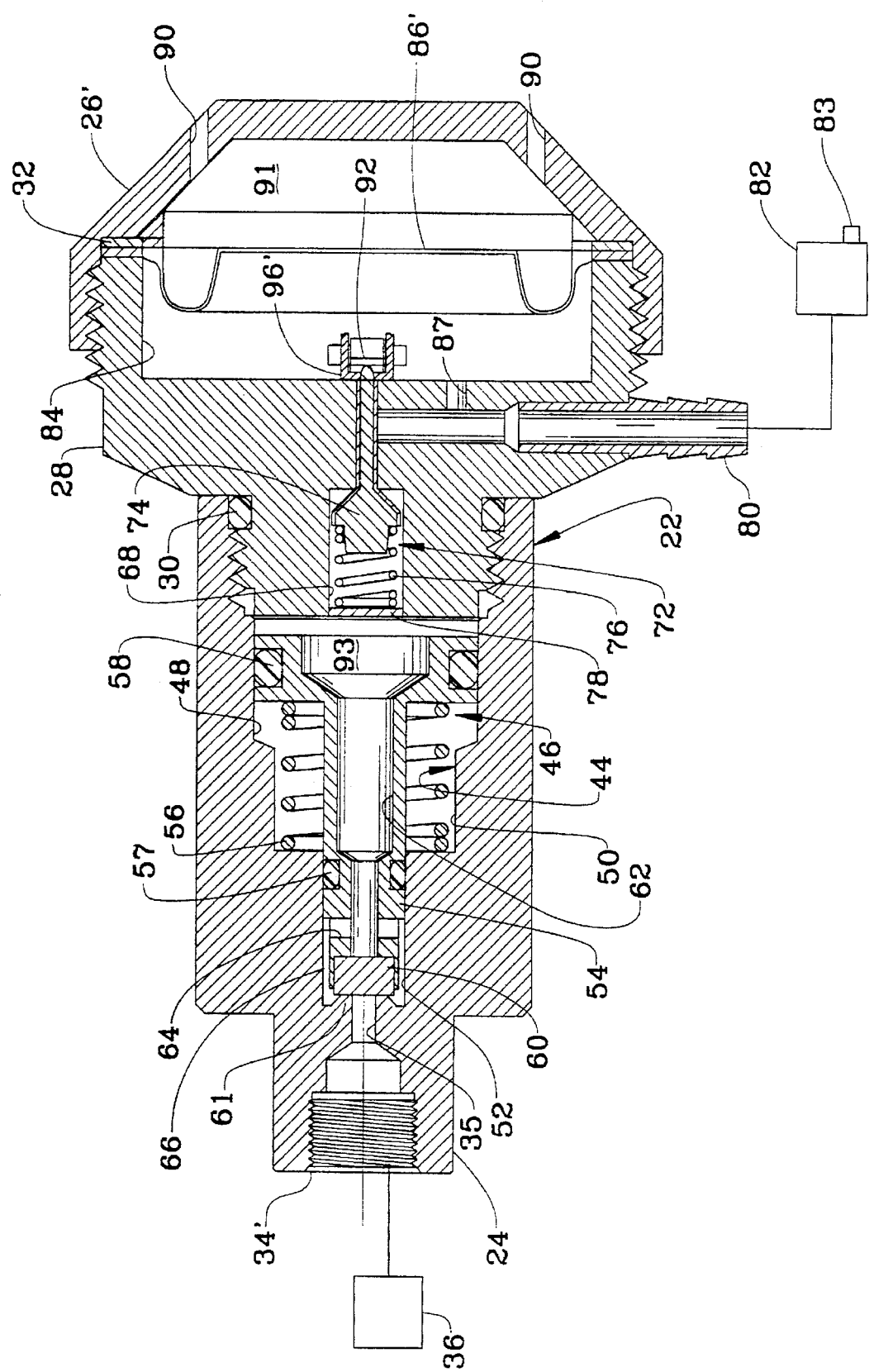
FIG. 4 is a longitudinal cross-sectional view of the instrument calibrating demand flow regulator shown in FIG. 3 taken along the section line 4—4.

FIGS. 3 and 4 illustrate an alternative embodiment of the instrument calibrating demand flow regulator of the present invention in which elements corresponding to those illustrated and described with respect to FIGS. 1 and 2 are designated by like reference numerals. In this alternative embodiment, the second housing end section 26' is conical in shape to define a slightly larger first space 91 that communicates with the atmosphere by way of the throughholes 90. In addition, each of the lever elements 92', 94' is mounted on its own respective mounting structure 96', with each of the mounting structures 96' being connected to the intermediate housing section 28 by way of the connecting screws 98.

In addition, the flexible diaphragm 86' is provided with an annular recess 87, 85. This configuration of the diaphragm 86' tends to be more sensitive to pressure differentials on either side of the diaphragm 86' and so the sensitivity of the regulator is increased. On the other hand, the sensitivity of the instrument can also be increased by mounting the lever elements in the manner shown in the embodiment of FIGS. 1 and 2 where the pivot point for the first lever member 92 is located very close to the end of the poppet 74.

In the embodiment shown in FIGS. 3 and 4, the inlet 34' that is connected to the calibration gas source is internally threaded rather than externally threaded as shown in the first embodiment. By utilizing an appropriately sized adaptor element having one end adapted to be threaded with the internally threaded inlet 34' and the opposite end suitably sized to connect to the corresponding connection element on the calibration gas source, the instrument calibrating demand flow regulator shown in FIGS. 3 and 4 can be used in conjunction with a wide variety of different calibration gas sources.

The instrument calibrating demand flow regulator of the present invention is highly advantageous in a variety of different respects. In response to the demand requirements of the instrument to be calibrated, the instrument calibrating demand flow regulator provides the exact amount of calibration gas needed. Upon disconnection of the instrument from the regulator, the regulator automatically shuts off and thus eliminates the possibility that calibration gas will be needlessly wasted. The instrument calibrating demand flow regulator is advantageously compact and can be made rather light-weight. The regulator can be made partially or entirely of aluminum with parts such as the diaphragm, the cover on the poppet and the various seals being made of elastomer material. Also, it possesses a low dead volume and a relatively quick response time. Further, through use of an instrument calibrating demand flow regulator in accordance with the present invention, the need for time consuming and complex operator training is eliminated. It is also envisioned that by employing an appropriate valving system and instrument control system, unattended automatic calibration of the instrument can be effected.

In a typical use of the instrument calibrating demand flow regulator of the present invention, the calibration gas source would be in the form of a cylinder containing the gas. It is envisioned, however, that the instrument calibrating demand flow regulator can be used in other ways. For example, the instrument calibrating demand flow regulator can be directly and permanently connected to the line providing the calibration gas. The instrument to be calibrated can then be connected to the outlet of the regulator and appropriately tested and calibrated.

The present invention is useful in conjunction with the calibration of a wide variety of instruments. For example, the instrument calibrating demand flow regulator can be used in connection with the calibration of instruments used to detect carbon monoxide, methane, hydrogen sulfide, and most any other instruments used in connection with industrial hygiene. Thus, the calibration gas sources with which the instrument calibrating demand flow regulator can be used include sources containing carbon monoxide, methane, hydrogen sulfide and a wide variety of other gases.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

What is claimed is:

1. Calibration system for calibrating an instrument, comprising:
   a source of calibration gas;
   a housing having an interior, said housing being provided with an inlet connected to the source of calibration gas, and an outlet for connection to the instrument to be calibrated;
   a movable element disposed within the interior of the housing and movable in response to a pressure differential on opposite sides of the movable element;
   a demand flow valve element disposed within the interior of the housing to form a first space within the interior between the movable element and the demand flow valve element;
   a pressure regulating valve device disposed within the interior of the housing to form a second space within the interior between the demand flow valve element and the pressure regulating valve device;
   said demand flow valve element being movable between one position in which gas flow between said first space and said second space is prevented and a second position in which gas flow between said first space and said second space is permitted, said demand flow valve element being operatively associated with said movable element so that movement of the movable element caused by a pressure differential across the movable element results in movement of the demand flow valve element from the first position to the second position, said pressure regulating valve device being movable between a first position in which the flow of calibration gas into the second space is prevented and a second position in which the flow of calibration gas into the second space is permitted, said pressure regulating valve device being movable from the first position to the second position in response to the pressure in the second space being reduced to a predetermined level after said demand flow valve has moved away from said first position.

2. Calibration system according to claim 1, including a contents gauge connected to the inlet for identifying the pressure at the source of calibration gas.

3. Calibration system according to claim 1, wherein said pressure regulating valve device includes a piston having a longitudinally extending bore possessing a varying internal diameter.

4. Calibration system according to claim 3, including a first spring for urging the piston in a direction towards the demand valve device.

5. Calibration system according to claim 3, wherein said piston is slidably disposed in a bore in the housing and includes a cross bore transverse to the longitudinally extending bore and intersecting the longitudinally extending bore, and a space between an outer periphery of the piston at one end portion of the piston and an inner surface of a portion of the bore in the housing that receives the one end portion of the piston so that calibration gas flowing through the inlet flows through said space, through said cross bore and into the longitudinally extending bore in the piston.

6. Calibration system according to claim 1, wherein said demand flow valve element includes a poppet and a spring for urging the poppet towards the first space and into engagement with a valve seat.

7. Calibration system according to claim 6, including two pivotably mounted lever elements disposed in the first space, one of said lever elements being moved in response to movement of the movable element, the other lever element being moved in response to movement of the one lever element to contact the poppet and move the poppet to the second position.

8. Calibration system according to claim 6, wherein the housing includes a wall located between the first and second spaces, said wall being provided with a through hole through which extends a portion of the poppet.

9. Instrument calibrating demand flow regulator for providing a demanded amount of calibration gas from a calibration gas source to an instrument to be calibrated to permit calibration of the instrument, comprising:
a housing having an interior, said housing being provided with an inlet for connection to the calibration gas source and an outlet for connection to the instrument to be calibrated;
a pressure regulating valve device positioned within the interior of the housing for regulating the pressure of the calibrated gas entering the interior of the housing through the inlet; and
a demand flow valve device for delivering calibration gas to the outlet of the housing upon demand by a pump operatively associated with the instrument.

10. Instrument calibrating demand flow regulator according to claim 9, wherein said housing includes a pressure gauge port for connecting a pressure gauge to the housing which identifies the pressure of the calibration gas source, said pressure gauge port being in fluid communication with the inlet in the housing.

11. Instrument calibrating demand flow regulator according to claim 9, including a pressure gauge connected to the housing and in fluid communication with the inlet in the housing for identifying the pressure of the calibration gas source.

12. Instrument calibrating demand flow regulator according to claim 9, wherein the maximum flow through the instrument calibrating demand flow regulator is 6.0 liters/min.

13. Instrument calibrating demand flow regulator according to claim 9, wherein said demand flow valve device includes a poppet and a movable diaphragm between which is defined a space, and first and second pivotally mounted lever members disposed in the space.

14. Instrument calibrating demand flow regulator according to claim 13, wherein said outlet is connected to said space, said first lever member being pivotable in response to movement of the diaphragm resulting from a reduction in pressure within the space to below atmospheric, the second lever member being pivotable upon being contacted by the first lever member to thereby contact the poppet and move the poppet to a position which effects movement of the pressure regulating valve device to permit passage of calibration gas from the inlet to the outlet.

15. Instrument calibrating demand flow regulator according to claim 9, wherein said pressure regulating valve device includes a movable piston which is provided with a longitudinally extending bore extending from adjacent one end of the piston towards an opposite end of the piston.

16. Instrument calibrating demand flow regulator according to claim 15, wherein said piston is slidably disposed in a bore in the housing and includes a cross bore transverse to the longitudinally extending bore and intersecting the longitudinally extending bore, and a space between an outer periphery of the piston at one end portion of the piston and an inner surface of a portion of the bore in the housing that receives the one end portion of the piston so that calibration gas flowing through the inlet flows through said space, through said cross bore and into the longitudinally extending bore in the piston.

17. Method of calibrating an instrument, comprising:
connecting an inlet of an instrument calibrating demand flow regulator to a calibration gas source, the instrument calibrating demand flow regulator including a pressure regulating valve device positioned within an interior of a housing for regulating the pressure of calibration gas entering the interior of the housing through the inlet, and a demand flow valve device positioned within the interior of the housing for delivering calibration gas to an outlet of the instrument calibrating demand flow regulator upon demand by a suction pump associated with the instrument;
connecting an instrument to be calibrated to the outlet of the instrument calibrating demand flow regulator so that the pump of the instrument to be calibrated draws calibrated gas through the instrument calibration demand flow regulator.

18. Method according to claim 17, wherein said demand flow valve device includes a poppet and a movable diaphragm between which is defined a space, and first and second pivotally mounted lever elements disposed within the space, the diaphragm moving upon connection of the instrument to the outlet during operation of the suction pump, the movement of the diaphragm causing pivoting movement of the second lever element which causes pivoting movement of the first lever element, the pivoting movement of the second lever element causing the second lever element to contact and axially move the poppet.

19. Method according to claim 18, wherein said pressure regulating valve device includes a piston provided with a bore extending from adjacent one end of the piston to adjacent an opposite end of the piston, the piston moving upon axial movement of the poppet to cause calibration gas to flow from the inlet to the outlet.

20. Method according to claim 17, wherein the maximum flow of calibration gas through the instrument calibrating demand flow regulator is 6.0 liters/min.

* * * * *